United States Patent
Bulgarelli et al.

(10) Patent No.: US 12,427,101 B2
(45) Date of Patent: Sep. 30, 2025

(54) FRAGRANCE-CONTAINING MICROPARTICLES

(71) Applicant: Givaudan SA, Vernier (CH)

(72) Inventors: Nelly Bulgarelli, Loveland, OH (US); Ian Michael Harrison, Poissy (FR); Paula Maria Nogueira Ambrogi, São Paulo (BR); Nicolò Manfredini, Pugliola di Lerici (IT); Matteo Maraldi, Milan (IT); Massimo Morbidelli, Morcote (CH); Davide Moscatelli, Arese (IT); Umberto Capasso Palmiero, Zurich (CH); Mattia Sponchioni, Vaiano Cremasco (IT); Giuseppe Storti, Lodi (IT)

(73) Assignee: Givaudan SA, Vernier (CH)

( * ) Notice: Subject to any disclaimer, the term of this patent is extended or adjusted under 35 U.S.C. 154(b) by 448 days.

(21) Appl. No.: 18/001,283

(22) PCT Filed: Jul. 23, 2021

(86) PCT No.: PCT/EP2021/070661
§ 371 (c)(1),
(2) Date: Dec. 9, 2022

(87) PCT Pub. No.: WO2022/018259
PCT Pub. Date: Jan. 27, 2022

(65) Prior Publication Data
US 2023/0233442 A1    Jul. 27, 2023

(30) Foreign Application Priority Data
Jul. 23, 2020    (EP) .................................... 20290056

(51) Int. Cl.
| | | |
|---|---|---|
| *A61K 8/02* | (2006.01) | |
| *A61K 8/41* | (2006.01) | |
| *A61K 8/46* | (2006.01) | |
| *A61K 8/55* | (2006.01) | |
| *A61K 8/81* | (2006.01) | |
| *A61K 8/86* | (2006.01) | |
| *A61Q 5/02* | (2006.01) | |
| *A61Q 5/12* | (2006.01) | |
| *A61Q 13/00* | (2006.01) | |

(52) U.S. Cl.
CPC .............. *A61K 8/8152* (2013.01); *A61K 8/55* (2013.01); *A61Q 5/02* (2013.01); *A61Q 5/12* (2013.01); *A61Q 13/00* (2013.01); *A61K 2800/56* (2013.01)

(58) Field of Classification Search
None
See application file for complete search history.

(56) References Cited

U.S. PATENT DOCUMENTS

| | | | |
|---|---|---|---|
| 2004/0091445 A1 | 5/2004 | Dykstra et al. | |
| 2004/0138093 A1* | 7/2004 | Brain ................... | A61K 8/8158 512/4 |
| 2005/0238608 A1 | 10/2005 | Ouali et al. | |

FOREIGN PATENT DOCUMENTS

WO    9963956 A1    12/1999

OTHER PUBLICATIONS

Sugiyama et al., Poly. J., 1994, 26(5), pp. 561-569 (Year: 1994).*
Zhang et al.., J. Appl. Polm. Sci., 2016, vol. 133, 44136 (7 pages) (Year: 2016).*
International Search Report for App. No. PCT/EP2021/070661 dated Nov. 19, 2021.
Written Opinion for App. No. PCT/EP2021/070661 dated Nov. 19, 2021.
Yuanfeng Pan, et al., Hydrophobic modification of cellulose fibres by cationic-modified polyacrylate latex with core-shell structure, Cellulose, Dec. 4, 2012, pp. 485-494, vol. 20, Springer.

* cited by examiner

*Primary Examiner* — Brian Gulledge
(74) *Attorney, Agent, or Firm* — Curatolo Sidoti & Trillis Co., LPA; Floyd Trillis, III; Salvatore A. Sidoti

(57) ABSTRACT

A fragrance-containing microparticle of water-insoluble polymeric material, the polymer having a glass transition temperature of from 0° C. to 50° C. and a zeta potential lying within the ranges −40 mV to −5 mV and +5 mV to +45 mV. The microparticles have enhanced substantivity to hair, resulting in a longer-lasting fragrance.

10 Claims, 9 Drawing Sheets

FRAGRANCE-CONTAINING MICROPARTICLES

CROSS REFERENCE TO RELATED APPLICATIONS

Figure 1:
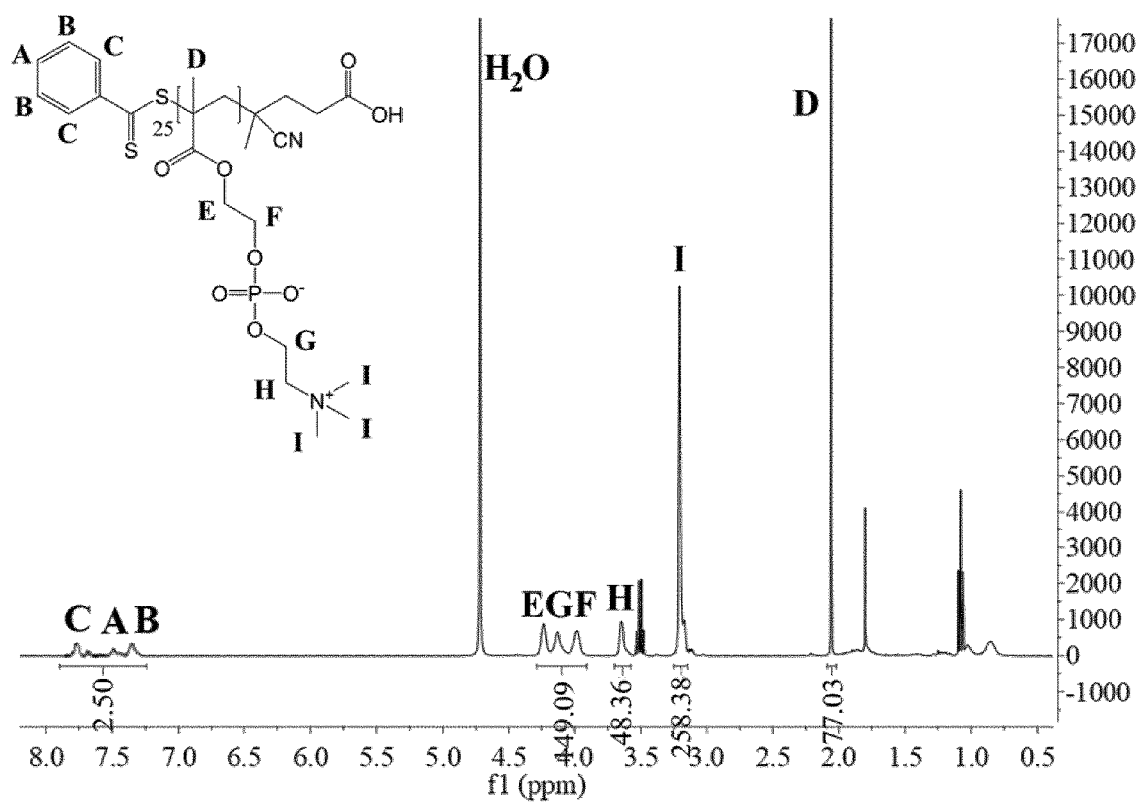

This application is a national stage application of International Application No. PCT/EP2021/070661, filed 23 Jul. 2021, which claims priority from European Patent Application No. 20290056.9, filed 23 Jul. 2020, both of which applications are incorporated herein by reference.

This disclosure relates to microparticles, and more particularly to their use in rinse-off hair care compositions.

By microparticles is meant particles having an average diameter range between 0.1 and 20 μm. The term covers any particle of this size range, and includes solid and porous particles and microcapsules of the core-shell variety with a polymeric shell surrounding a core of liquid fragrance.

Rinse-off hair care compositions are compositions applied to hair and then rinsed off; these include shampoos and conditioners. It is desired to leave a lasting fragrance on the hair after rinsing, and this has often been done by adding fragrance-containing microparticles to the compositions. These should remain on the hair and contribute a lasting fragrance.

The problem in the art has been providing a desirable degree of substantivity, that is, ensuring that a suitably large proportion of the microparticles remain on the hair after rinsing. Various methods have been tried, mainly involving the modification of the microparticle surfaces with substances with a higher degree of substantivity to hair than have the polymers from which the microparticles are formed. While this has gone some way to overcoming the problem, in that the proportion of microparticles remaining on the hair is higher, the proportion remains undesirably low, and a higher proportion is desirable.

It has now been found that the degree of substantivity of fragrance-containing microparticles to hair can be enhanced. There is therefore provided a fragrance-containing microparticle of water-insoluble polymeric material, the polymer having a glass transition temperature of from 0° C. to 50° C. and a zeta potential lying within the ranges −40 mV to −5 mV and +5 mV to +45 mV.

There is additionally provided a rinse-off hair care composition comprising fragrance-containing microparticles as hereinabove described.

There is further provided a method of conferring on hair a long-lasting fragrance, comprising treatment with a rinse-off hair care composition as hereinabove described.

The glass transition temperature (Tg) is a parameter well known to the polymer arts. It is the temperature at which a polymer changes from a "glassy" state to a "rubbery" state. The Tgs of polymer vary widely—for example, the rubber used in car tyres typically has a Tg of −70° C., whereas that of poly(methyl methacrylate) (Plexiglas™) is 105° C. The melamine-formaldehyde resins frequently used to provide the walls of fragrance-containing microparticles have Tgs typically of over 130° C.

For the purposes of this disclosure, it is essential that the microparticles have a positive or negative zeta-potential. It is important, as the data shows. The zeta-potential is a measure of the surface charge of the microparticles when dispersed in water. It is the potential difference between the dispersion medium and the stationary layer of fluid attached to the microparticle and it is measured by a zeta potential analyzer. The surface charge originates from charged species that are inherently present on the polymer of the microparticle, that are adsorbed or reacted on to the surface of the microparticles, or both of these possibilities. Typical examples of charged species include carboxylates, sulfonates, sulphates, phosphorus-based groups such as phosphonates or phosphates, quaternary ammonium and protonated amines. These groups may be provided by suitable compounds, for example sodium dodecyl sulfate, cetium trimethyl ammonium bromide, or by monomers contributing suitable groups, for example, the zwitterionic methacryloyloxyethylphosphorylcholine.

In particular embodiments:
The Tg is selected from the range 20° C. to 40° C., more particularly from 20° C. to 30° C.
The zeta-potential is selected from the range +30 to +45 mV.
The Tg is selected from the range 20° C. to 40° C., more particularly from 20° C. to 30° C., and the zeta-potential is selected from the range +30 to +45 mV:

The polymer used for the preparation may be any addition polymer that complies with the Tg requirements. Particular examples of suitable monomers are the esters of acrylic and methacrylic acids. Particular examples of suitable polymers include (meth)acrylate polymers such as poly(butyl methacrylate) and copolymers of methyl methacrylate and the butyl methacrylate with the desired Tg range. In such a copolymer, the methyl methacrylate (MMA) monomer content is 20% by weight maximum. In particular embodiments, the MMA content is 15%, 10% and 5% by weight, the balance being butyl methacrylate.

A further particular example of an acrylic monomer is 2-methacryloyloxyethylphosphorylcholine. This has the advantage, not only of providing a suitable polymer with the correct Tg, but also, as hereinabove mentioned, of providing a group that provides the resulting microparticle with a zeta-potential in one of the desired ranges. It may be used as a homopolymer, or as part of a copolymer with any other suitable (meth)acrylate monomer, particularly one or more of methyl methacrylate and butyl methacrylate.

In a particular embodiment, the polymer is a copolymer of methyl methacrylate and 2-methacryloyloxyethylphosphorylcholine, the methyl methacrylate (MMA) monomer content being 20% by weight maximum. In particular embodiments, the MMA content is 15%, 10% and 5% by weight, the balance being 2-methacryloyloxyethylphosphorylcholine.

It has been found that the combination of the relatively low Tg and the particular zeta-potential range provides microparticles with particularly good adherence to hair.

The fragrance in the microparticles may be any desired fragrance. It is known that certain polymers will interact with some fragrance ingredients, thus changing the nature of the fragrance as originally formulated, but this is well known and a fragrance can be formulated to compensate for this, using the normal skill and knowledge of the art.

The microparticles may be prepared by standard methods known to the art.

The microparticles may be incorporated into a rinse-off hair care formulation in the proportions normally used in the art. A typical proportion is from 0.01-1.0% by weight, particularly from 0.1-0.8%, more particularly from 0.3-0.8%, and even more particularly from 0.3-0.6%. Apart from the microparticles, the rinse-off hair care formulation may be formulated using the normal techniques and raw materials known to the art.

There is also provided a method of achieving a long-term fragrancing of hair, comprising the application of a hair care composition as hereinabove described.

The disclosure is further described with reference to the following figures and examples, which depict particular embodiments, and which are not intended to be in any way limiting on the scope of the disclosure.

THE FIGURES ARE AS FOLLOWS

FIG. 1: $^1$H-NMR spectra of PolyMPC performed on a Brooker Ultrashield 400 MHz spectrometer.

Figure 2:
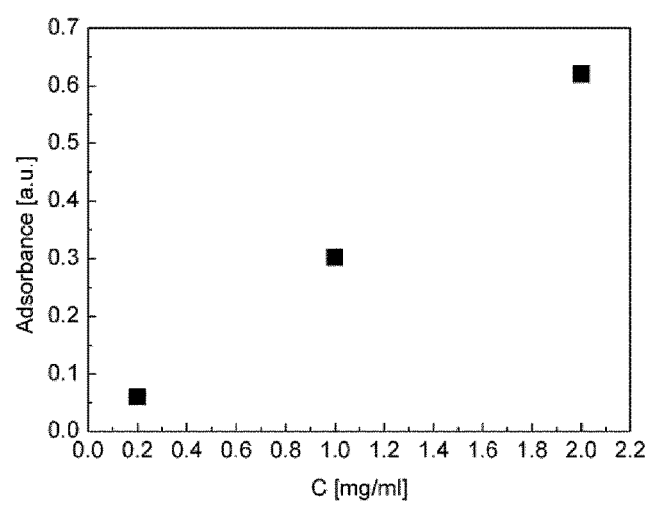

FIG. 2: Calibration curve in the case of sample BMA-MPC1.

Figure 3:
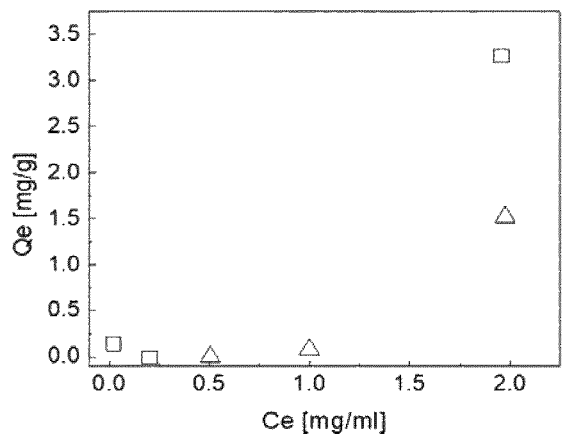

FIG. 3. Adsorption isotherm (Qe vs. Ce) of sample SDS-MMA1 (□) and SDS-BMA1 (Δ).

Figure 4A:
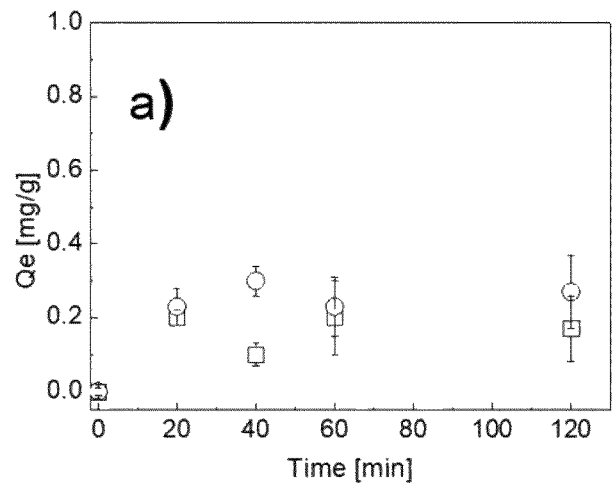

FIG. 4. Adsorption kinetics (Qe vs. time) of MMA-MPC1 (a) and BMA-MPC1 (b) at different values of initial particle concentration: 0.5 (□), 1 (○) and 2 (Δ) mg/ml.

Figure 5A:
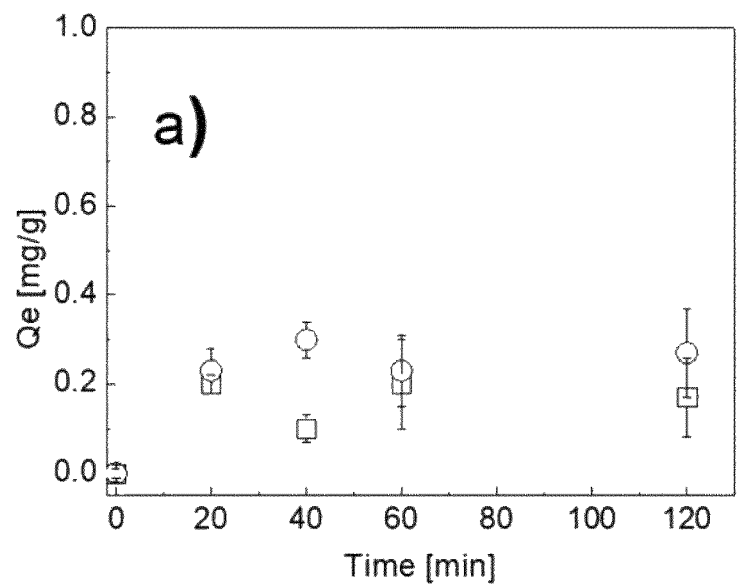
Figure 5B:
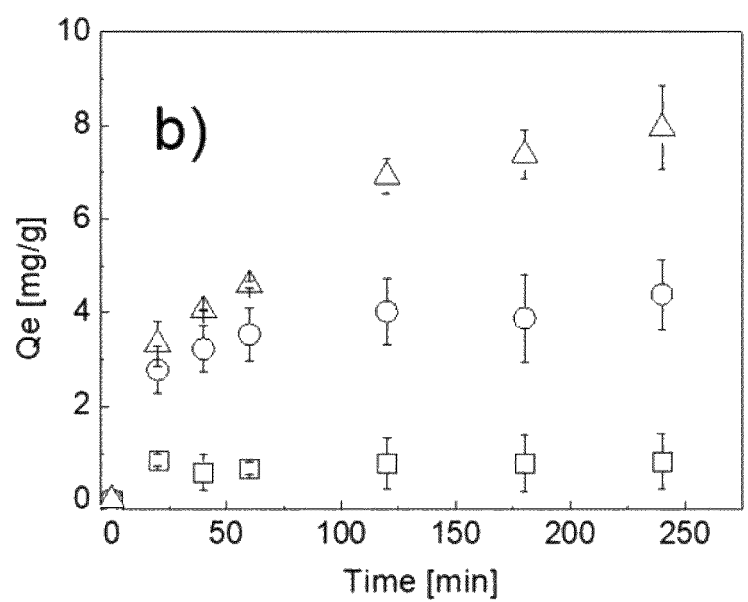

FIG. 5. Adsorption kinetics (Qe vs. time) of MMA-MPC1 (a) and BMA-MPC1 (b) at different values of initial particle concentration: 0.5 (□), 1 (○) and 2 (Δ) mg/ml.

Figure 6:
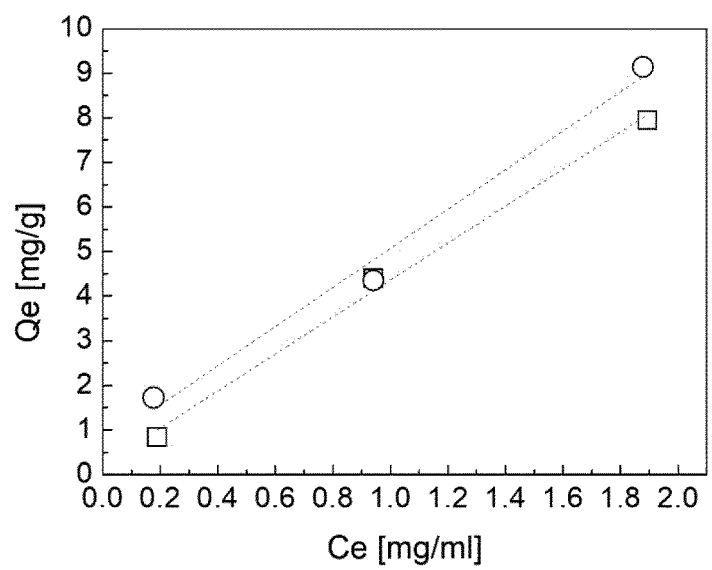

FIG. 6. Adsorption isotherms (Qe vs. Ce) for sample BMA-MPC1 in distilled (□) and tap (○) water, respectively.

Figure 7:
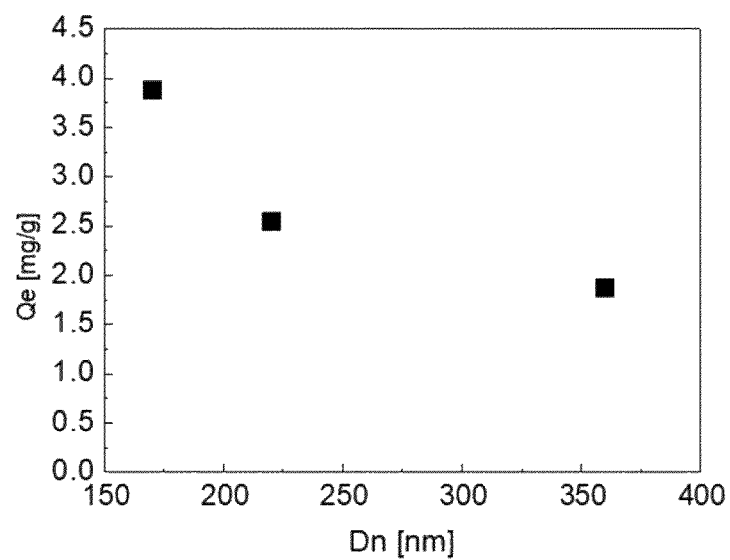

FIG. 7. Adsorbed amounts Qe as a function of particle diameter Dn for sample BMA-MPC1. Initial particle concentration of 1 mg/ml.

Figure 8:
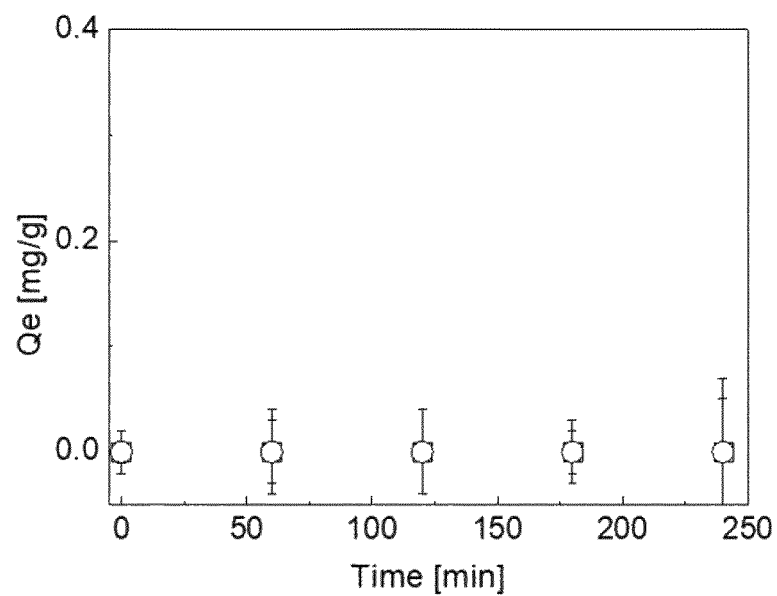

FIG. 8. Adsorption kinetics: Qe vs. time for sample BMA-PEG. Initial particle concentrations of 0.2 (□) and 2 (○) mg/ml.

Figure 9A:
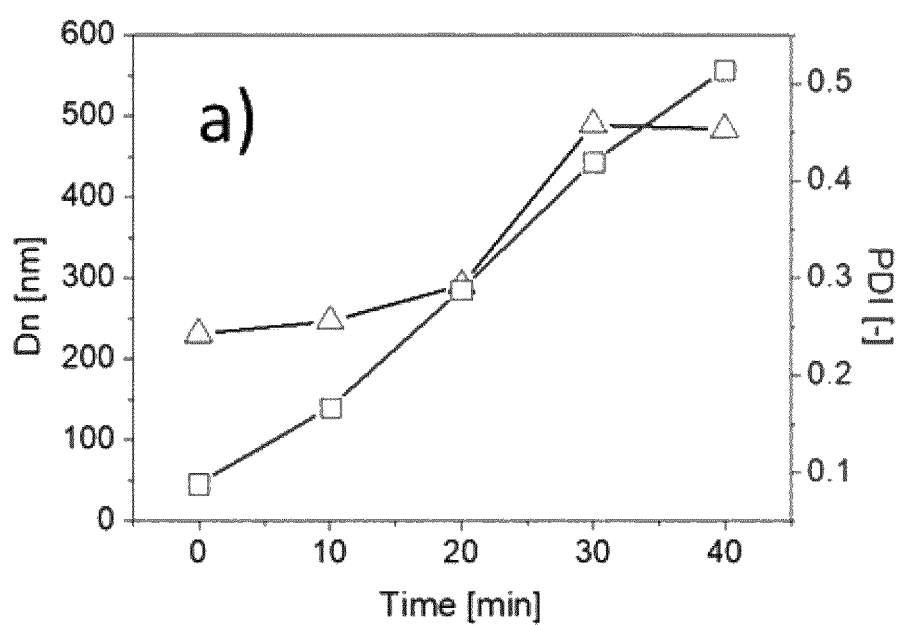
Figure 9:
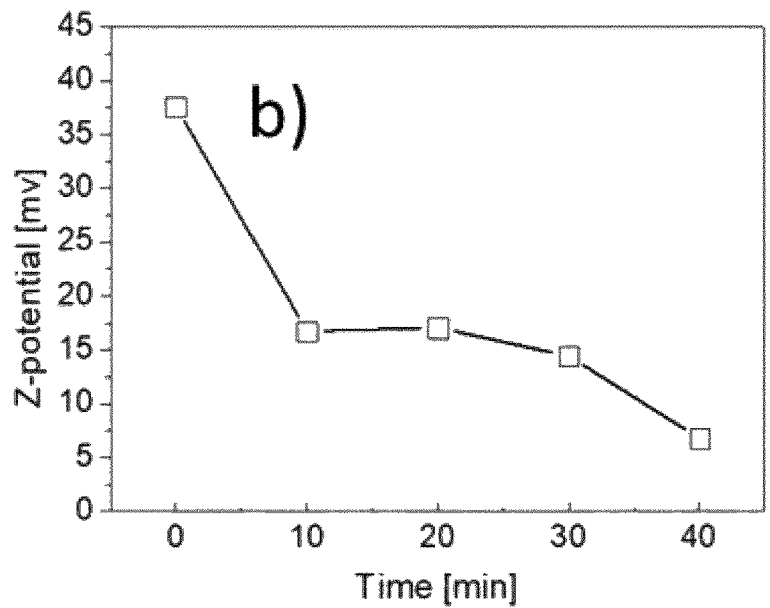

FIG. 9. a) Average particle diameter Dn (Δ) and PDI (□) vs. time for the batch adsorption experiment of sample MMA-CTAB1, b) ξ-potential as function of time for the batch adsorption experiment of sample MMA-CTAB1.

FIG. 10. Average particle size Dn (□, black) and PDI (□, blue) vs. time for the batch adsorption experiment of sample MMA-CTAB1 using hair pre-saturated by CTAB (a). Adsorption kinetics of MMA-CTAB1 (b) at 1 (○) and 2 (□) mg/ml (b). Stability of sample CTAB-BMA1 during adsorption: average particle diameter (Dn) vs Time and PDI vs Time (c).

Figure 11:
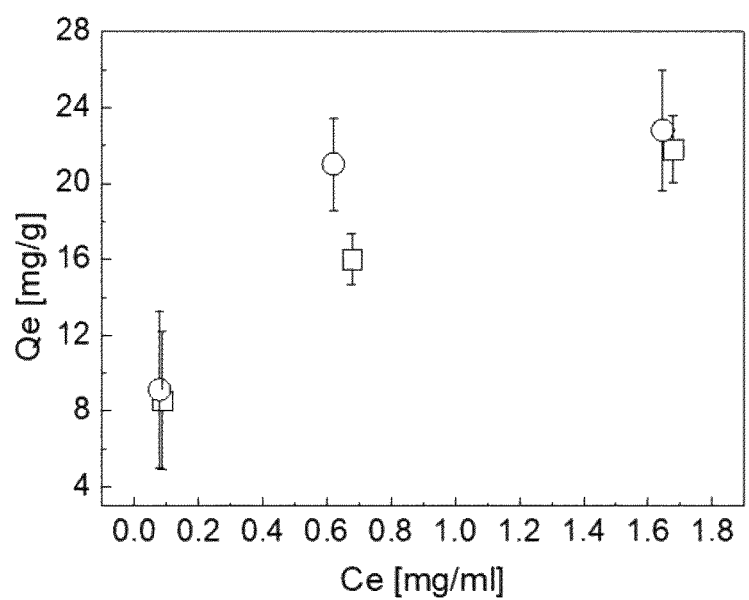

FIG. 11. Equilibrium isotherm: adsorbed amount Qe as a function of Ce for sample BMA-CTAB1 in distilled (○) and tap (□) water, respectively.

Figure 12:
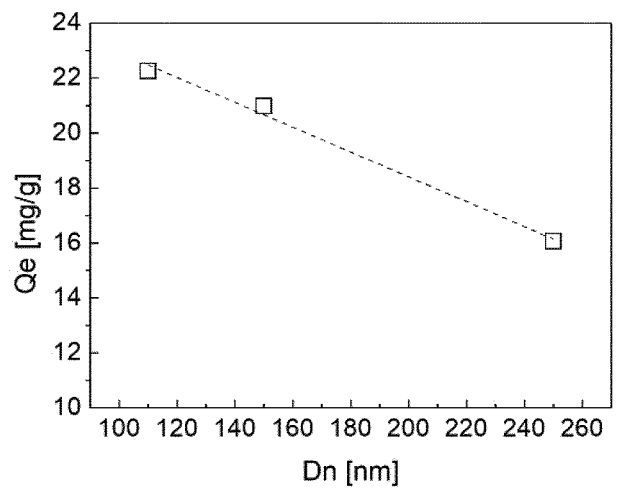

FIG. 12. Qe as function of Dn for BMA-CTAB particles tested at a concentration of 1 mg/ml.

Figure 13:
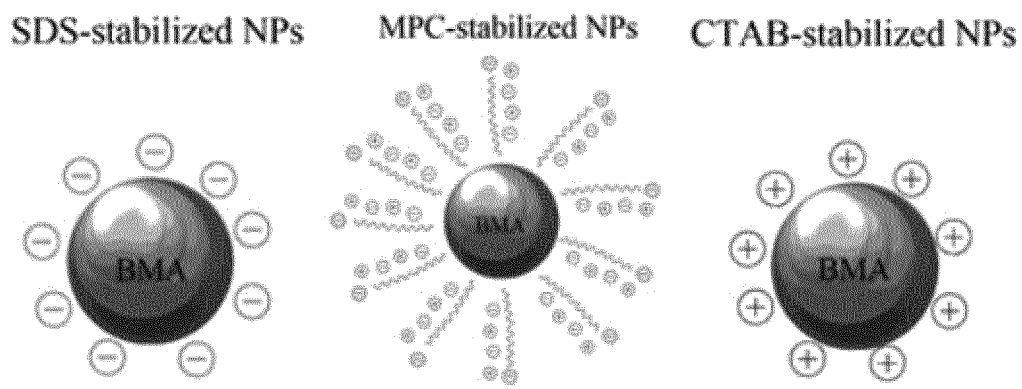
Figure 14A:
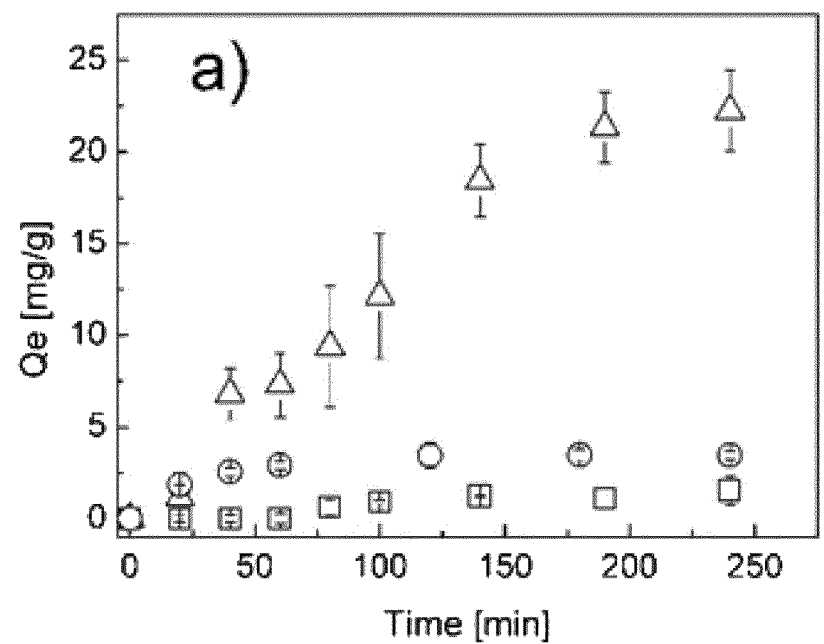
Figure 14B:
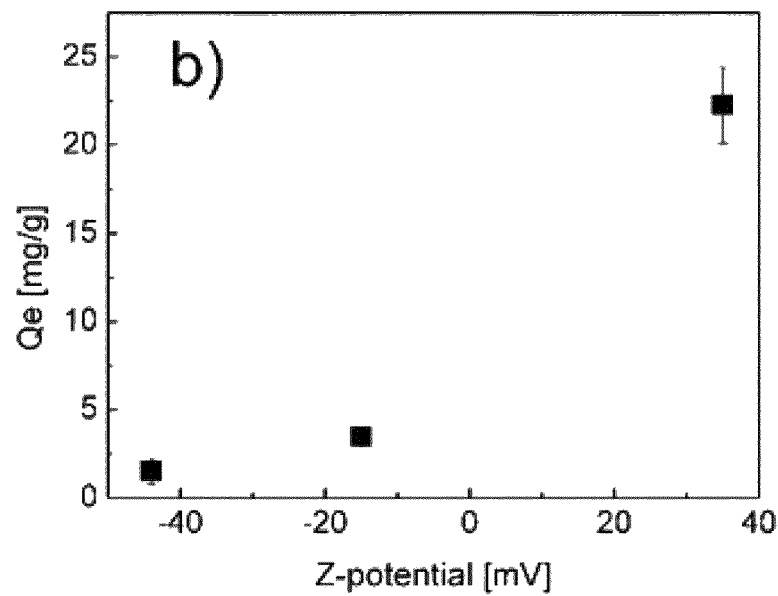

FIG. 13 Schematic representation of the three different BMA based particles, stabilized respectively from left to right by SDS, MPC and CTAB FIG. 14. Adsorption kinetics of SDS-BMA1 (□) and BMA-MPC1 (○) and BMA-CTAB1 (Δ) tested at a concentration of 1 mg/ml (a), trend of Qe as function of ξ-potential (b).

1. MATERIALS

Methyl methacrylate (MMA, 99%, MW=100.12, Sigma-Aldrich),
butyl methacrylate (BMA, 99%, MW=142.20 Sigma-Aldrich),
2-methacryloyloxyethylphosphorylcholine (MPC, 97%, MW=295.27, Sigma-Aldrich)
sodium dodecyl sulfate (SDS, 90%, MW=288.372, Merck),
poly(ethylene glycol) methyl ether methacrylate (PEG_1000, average MW=1000, Sigma-Aldrich),
hexadecyl-trimethyl-ammonium bromide (CTAB, 98%, MW=364.45, ABCR),
potassium peroxodisulfate (KPS, 99%, MW=270.32, Sigma-Aldrich),
4,4'-Azobis(4-cyanovaleric acid) (ACVA, >98%, MW=280.28, Sigma-Aldrich),
2,2'-Azobis(2-methylpropionamidine) dihydrochloride (alpha-alpha, 97%, MW=271.19, Sigma-Aldrich),
sodium carbonate (Na$_2$CO$_3$, 99.5-100.5%, MW=105.99, Sigma-Aldrich),
Ethylene glycol dimethacrylate (EGDMA, 98%, MW=198.22, Sigma-Aldrich),
4-cyano-4-(phenylcarbonothioylthio)pentanoic acid (CPA, 97%, MW=279.38, Sigma-Aldrich),
[2-(Methacryloyloxy)ethyl]trimethylammonium chloride solution (MADQUAT, 80 wt % in H$_2$O, MW=207.70, Sigma-Aldrich),
ethanol absolute (EtOH, >99%, MW=46.07, Sigma Aldrich)
All solvents were from Sigma-Aldrich at analytical-grade purity.

2. SYNTHESIS OF PARTICLES(PARTICLES)

2.2.1 Negative Particles

Highly-negative particles were synthesized via free radical emulsion polymerization (FRPe) of either MMA or BMA, leading to high and low Tg polymers respectively, and using SDS as surfactant. A monomer concentration of 5% w/w with respect to the solvent was used. The surfactant to monomer weight fraction was tuned in order to produce particles of different size (Table A1 below) while the initiator (KPS) concentration was maintained constant and equal to 1% with respect to monomer.

In a typical procedure, 25 mg of SDS was dissolved in 45 g of deionized (DI) water in a flask equipped with a magnetic stirrer. 2.5 g of MMA was added dropwise to the solution with strong stirring. The flask was then sealed with a rubber stopper and the mixture purged by bubbling nitrogen for 20 minutes before heating to 80° C. in a thermostated oil bath. After an equilibration time of 10 minutes, 25 mg of KPS dissolved in 2.5 g of DI water was injected into the flask and the reaction was allowed to occur for 7 hours at 80° C. and with a stirring rate of 300 rpm. At the end of the reaction, the monomer conversion was evaluated via thermo-gravimetric analysis by evaporating water in an Ohaus mb120 moisture analyzer. The particle size distribution and ξ-potential were measured by dynamic light scattering (DLS) using a Malvern Zetasizer Nano ZS.

TABLE A1

Main properties of the highly charged ad neutral particles synthesized in this work (average particle size, Polydispersity Index (PDI), surface charge (ζ-potential) and weight percentage of surfactant.

| Sample | Monomer | Size [nm] | PDI [—] | ζ-pot [mV] | Surfactant [wt %] |
|---|---|---|---|---|---|
| MMA-SDS1 | Methyl Methacrylate | 115 | 0.091 | −43 | 1 |
| MMA-SDS2 | Methyl Methacrylate | 208 | 0.124 | −39 | 0.75 |
| BMA-SDS1 | Butyl Methacrylate | 185 | 0.04 | −44 | 1 |
| BMA-SDS2 | Butyl Methacrylate | 205 | 0.03 | −43 | 0.75 |
| BMA-SDS3 | Butyl Methacrylate | 290 | 0.08 | −39 | 0.5 |
| BMA-PEG | Butyl Methacrylate | 360 | 0.15 | +1.2 | 1 |
| MMA-CTAB1 | Methyl Methacrylate | 240 | 0.014 | +43 | 1 |
| MMA-CTAB2 | Methyl Methacrylate | 440 | 0.037 | +37 | 0.5 |
| BMA-CTAB1 | Butyl Methacrylate | 110 | 0.09 | +40 | 1 |
| BMA-CTAB2 | Butyl Methacrylate | 150 | 0.04 | +35 | 0.75 |
| BMA-CTAB2 | Butyl Methacrylate | 250 | 0.03 | +38 | 0.5 |

Moderately negative particles were synthesized via a 2-step reversible addition-fragmentation chain transfer (RAFT) polymerization. More specifically, a hydrophilic polyMPC macromolecular chain transfer agent (macro CTA) was synthesized in solution using a mixture of ethanol/acetic buffer (10 mM, pH=4.5) 50/50 v/v as solvent. 21 mg (76 µmol) of CPA, 7 mg (25 µmol) of ACVA (i.e. CPA/ACVA=3 mol/mol), and 1.119 g (3.8 mmol) of MPC (i.e. MPC/CPA=50 mol/mol) were dissolved in 5 ml of the mixture ethanol/acetic buffer previously described. The solution was purged with nitrogen for 10 minutes and left to react at 65° C. for 24 h in an oil bath under stirring. The mixture was then precipitated in acetone and the final polymer was recovered and stored at −20° C. Monomer degree of polymerization ($n_{NMR}$) was evaluated via $^1$H-NMR (FIG. 1) before and after the purification (10 mg were dissolved in a 0.8 mg of $D_2O$ and analyzed on a Bruker 400 MHz spectrometer) according to eq. A1.

$$n_{NMR} = \left(\frac{\frac{E+G+F}{6}}{\frac{A+B+C}{5}}\right) * X_{MPC} \quad (A1)$$

where A, B and C the area of the peaks attributed to the aromatic protons of the RAFT agent, while E, F and G are the area of the peaks referred to the protons of the MPC molecule. The MPC conversion, $X_{MPC}$, in Equation A1 was assumed equal to 1, due to the absence of vinyl protons in the range 5.5-6.5 ppm in the NMR spectrum.

The monomer conversion (X) was assumed almost complete as indicated by the absence of the vinyl protons in the range 5.5-6.5 ppm in FIG. 1. The results are listed in Table A2 below. The polyMPC macro CTA was subsequently chain-extended via RAFT emulsion polymerization with either MMA or BMA to obtain amphiphilic block copolymers self-assembled into particles. The molar ratio between the monomer and the macro CTA (n) was varied in the range 2000-6000, in order to obtain particles with different size, as listed in Table A3 in Appendix. As an example, for the synthesis of the BMA-MPC2, 46.7 mg (ξ3 µmol) of polyMPC, 2.20 mg of EGDMA and 0.312 mg (1.1 µmol) of ACVA (i.e. polyMPC/ACVA=3 mol/mol) were dissolved in 20 ml of a mixture of ethanol/acetic buffer (10 mM, pH=4.5) 20/80 v/v in a 50 ml round bottom flask. Then 0.95 g (6.6 mmol) of BMA (i.e. BMA/polyMPC=2000 mol/mol) were poured in the reactor, the two phases were purged with nitrogen for 10 minutes and left to react for 7 hours at 70° C. under stirring. At the end of the reaction, the latex conversion was evaluated via thermo-gravimetric analysis and the particle size and ξ-potential by DLS.

TABLE A2

Conversion and number-average degree of polymerization (measured by NMR) of the MPC-based surfmer.

| Sample | Monomer | Conversion (X) [%] | $n_{NMR}$ [—] |
|---|---|---|---|
| PolyMPC | methacryloyloxyethylphosphorylcholine | 100 | 52 |

2.2.2 Neutral Particles

Neutral particles were synthesized via FRPe using PEG_1000 as steric surfmer, behaving both as surfactant and monomer. 25 mg of PEG_1000 was dissolved in 45 g of deionized (DI) water in a flask equipped with a magnetic stirrer. 2.5 g of BMA was added to the solution under strong stirring. The flask was then sealed with a rubber stopper and the mixture purged by bubbling nitrogen for 20 minutes before heating to 80° C. After an equilibration time of 10 minutes, 25 mg of KPS dissolved in 2.5 g of DI water were injected in the flask and the reaction was let to occur for 7 hours at 80° C. and with a stirring rate of 300 rpm. The particle suspension was characterized via DLS in terms of particle size distribution and surface ξpotential.

2.2.3 Positive Particles

Highly positive particles were synthesized via FRPe of either MMA or BMA using CTAB as surfactant. The synthesis procedure is the same as for highly negative or neutral particles but CTAB was used instead of SDS or PEG_1000, respectively.

2.3 Hair Preparation

Swatches of brown long hair (Caucasian type) were purchased from Kerling GmbH. For the cleaning process, the hair swatch was soaked in a 10% w/w SDS aqueous solution for 10 minutes and massaged by hand for 2 minutes. Then, the swatch was rinsed in tap water and squeezed along its full length between two fingers. The hair were left overnight in an ethanol/water 50/50 v/v mixture, rinsed again with water, and finally dried.

2.4 Adsorption Experiments 0.4 g of hair, cut in 2-3 cm long pieces, and 30 ml of particle dispersion at the selected concentration were put in a beaker equipped with a magnetic stirrer. The system was sealed with a plastic film (Parafilm M) to prevent water evaporation and left under gentle stirring (50 rpm). Different particle concentrations were explored, ranging from 0.02 mg/ml to 2 mg/ml. Samples of 1 ml of liquid phase were taken at different times during the experiment. Such samples were analysed via DLS to assess the particle stability, while the residual particle concentration in the liquid phase was determined from the sample absorbance measured at 500 nm using a Jasco V-630 UV-Vis spectrometer according to Equation 1:

$$C(t) = C_0 \frac{\text{Abs}(t)}{\text{Abs}_0} \quad (1)$$

where $C_0$ is the initial particle concentration and Abs(t) and $\text{Abs}_0$ are the sample absorbances measured at time t and time zero, respectively. The assumption of linear relationship between particle concentration and absorbance measured by UV-Vis was previously verified for every type of particles inside the experimental range of concentrations, as shown in FIG. 2. Note that, after the analyses, all of the samples were put back into the beaker to prevent excessive volume variation during the experiment. The adsorbed mass of particles on hair was evaluated from the absorbance signal through Equation 2:

$$Q_e(t) = \frac{VC_0}{m_{hair}}\left(1 - \frac{\text{Abs}(t)}{\text{Abs}_0}\right) \quad (2)$$

where V is the volume of the liquid phase (constant for all experiments and equal to 30 ml), $C_0$ the initial mass concentration of particles, $Q_e(t)$ the adsorbed mass of particles per unit mass of hair [mg/g] at time t, $m_{hair}$ the overall mass of hairs (0.4 g in all experiments) and Abs(t) and $\text{Abs}_0$ the absorbance measured at 500 nm at time t and time zero, respectively. At very long time, equilibrium conditions have been assumed and the relevant adsorption isotherm was built for every examined system. All the adsorption experiments were carried out in triplicates for a maximum duration of 4 hours.

3. RESULTS

Different types of particle were synthesized in order to investigate the influence of important physico-chemical properties over their adsorption on human hair. Specifically, particle surface charge (ξpotential), average particle size (Dn), and the glass transition temperature (Tg) of the polymer were studied. Namely, for each value of surface charge (ranging from highly negative to highly positive), the effect of the polymer Tg on the adsorption behavior was analyzed. Furthermore, since for each type of particles the batch experiments were carried out at the smallest size (around 100 nm), the impact of the particle size was explored in the most promising cases.

3.1 Highly Negative Particles

Highly negative particles were synthesized via FRPe of either MMA (i.e. high Tg) or BMA (i.e. low Tg) using SDS as surfactant. As reported in Table A1 above, these particles proved to be stable and monodisperse as confirmed by the low values of the Polydispersity Index (PDI). This is due to the selected method of synthesis: indeed, emulsion polymerization is a well-established polymerization technique able to provide high conversion and efficient control of the particle size distribution. Furthermore, the particles showed ξpotentials significantly negative, in the range −39 to −45 mV) as expected when using an anionic emulsifier such as SDS.

The adsorption kinetic of the particles on hair was analyzed at different particle concentrations, ranging from 0.02 mg/ml to 2 mg/ml. These measurements were performed using both types of polymer, with high and low glass transition temperature (Tg) and comparable size. The values of adsorbed mass of particles per unit mass of hair [mg/g] at equilibrium (i.e. after long enough contact time) are shown in FIG. 3 as a function of the particle concentration in solution (FIG. 4a for methyl methacrylate, SDS-MMA1, and FIG. 4b for butyl methacrylate, SDS-BMA1).

The values of adsorbed mass of particles are quite small (a few mg per gram of hair) and this may be ascribed to the electrostatic repulsion between the particles and hair, which have been demonstrated to show, despite their heterogeneous nature, a net negative surface charge. Such electrostatic interaction is indeed the dominant interaction mechanism between these particles and hair. Actually, other aspects like polymer softness and lipophilicity affect the adsorption equilibrium at negligible extent. Finally, the shape of the isotherm suggests a non-favorable adsorption equilibrium, with fast increase of the adsorbed amount at large concentrations only.

3.2 Moderately Negative Particles

To achieve more favorable interaction between particles and hair, moderately negative particles were synthesized via the two-step synthesis described in subsection 2.2.2. This comprises the RAFT polymerization of MPC to obtain a hydrophilic macromolecular chain transfer agent (macro CTA) that is subsequently chain-extended via RAFT emulsion polymerization in water with either MMA or BMA. With this strategy, particles structurally composed of amphiphilic block copolymers can be obtained. In particular, the polyMPC portion of the copolymer is located at the particle surface, providing colloidal stability, while the polyMMA or polyBMA segments constitute the particle core. The RAFT polymerization employed in the synthesis of the copolymers enables a good control over the degree of polymerization for the polyMPC portion as well as for the lipophilic block of the copolymer, as confirmed by NMR analyses and reported in Table A2. Despite no net charge is expected for polyzwitterion stabilizers, the moderately negative ξ-potential (in the range −15-−20 mV, Table A3 below measured for these particles is ascribed to the carboxylic acid end-group of the CTA used in this work, which is almost completely deprotonated at neutral pH.

TABLE A3

Main properties of the moderately charged particles synthesized in this work (average particle size, Polydispersity Index (PDI), surface charge (ζ-potential) and weight percentage of surfactant.

| Sample | Monomer | Size [nm] | PDI [—] | ζ-pot [mV] | $n_{NMR}$ |
|---|---|---|---|---|---|
| MMA-MPC1 | Methyl Methacrylate | 110 | 0.07 | −19 | 6000 |
| BMA-MPC1 | Butyl Methacrylate | 170 | 0.06 | −20 | 2000 |
| BMA-MPC2 | Butyl Methacrylate | 220 | 0.08 | −15 | 3000 |
| BMA-MPC3 | Butyl Methacrylate | 370 | 0.03 | −21 | 6000 |

The particles synthesized via PISA proved to be stable and monodispersed, as confirmed by the PDI values in Table A3. As shown in the table, different particle sizes were produced by varying the molar ratio between monomer and macro CTA.

Once the size and surface charge of the particles were assessed, their adsorption on hair was analyzed at different particle concentrations in distilled water, once more ranging from 0.2 mg/ml to 2 mg/ml and using both types of polymers, with high and low glass transition temperature. In contrast to the previous case, the glass transition temperature of the polymer played an important role on the adsorption on hair, as depicted in FIG. 5. In fact, the softer particles made of BMA exhibited much larger adsorption than the harder counterparts made of MMA, whose adsorption was negligible. The different behavior could be most probably imputed to the larger chain mobility, and therefore softness, of the polymer at low Tg, which should result in stronger adhesion of the particles to the hair surface.

Since the particles MPC-BMA1 showed promising adsorption results, their stability and adsorption equilibrium were further assessed using tap water instead of distilled water. As shown in FIG. 6, the values of adsorbed mass of particles per unit mass of hair [mg/g] at equilibrium in the two media were comparable. During these experiments, good stability of the particle dispersion was verified at all concentrations, thus confirming quite insensitive adsorption behavior in the two different environments.

Another important parameter affecting the adsorption of polymer particles on hair is their size. Of course, at constant mass concentration of polymer, the specific surface of the particles (area per unit volume) increases at decreasing particle size. Then, large adsorption abilities are expected when smaller particles are considered. Actually, this expectation is supported by the results in FIG. 7, where the adsorbed mass of particles per unit mass of hair [mg/g] is plotted as a function of the particle diameter. Indeed, the reduction of particle diameter promotes a significant increase of adsorption on hair even inside the examined range, from 100 to 300 nm.

3.2 Neutral Particles

Neutral particles were synthesized via FRPe using PEG-1000 as surfmer and BMA as monomer. The key feature of the surfmer is its double bond, which enables chemical anchoring to the particles and prevents stabilizer depletion.

The particles stability is provided via steric stabilization mediated by the long PEG chains that extend from the surface. However, this same mechanism of stabilization is the main reason behind the complete absence of adsorption observed in FIG. 8 where data of adsorption kinetics are reported at two different concentrations. In a similar system, not only the electrostatic but also other possible types of interaction are suppressed by the steric hindrance of the stabilizer that results in the complete repulsion of the particles by hair. Furthermore, since the BMA-based particles should be the most adsorbing material according to the results discussed in the previous section, neutral particles were no longer synthesized and tested.

3.3 Highly Positive Particles

Figure 4B:
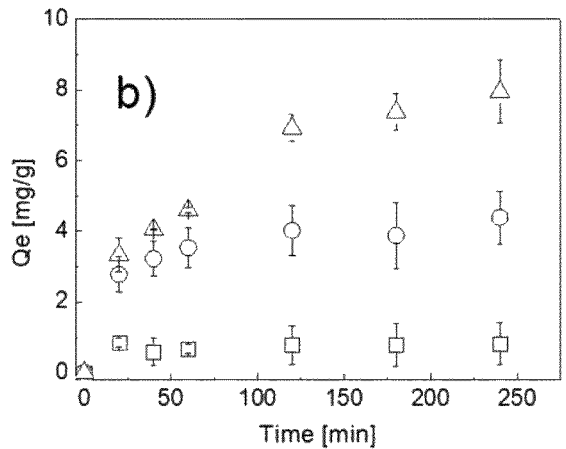
Figure 10A:
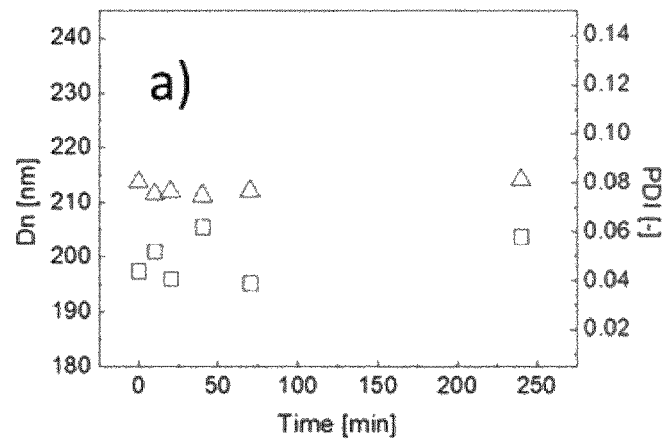
Figure 10B:
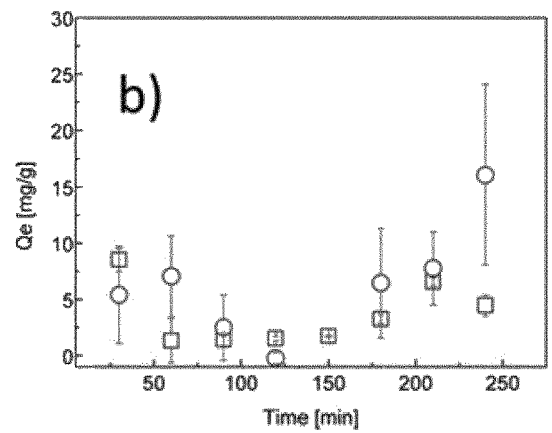

Highly positive particles have been synthesized via FRPe using the quaternary ammonium salt CTAB as surfactant. In this way, particles with absolute value of ξ-potential comparable to that of the highly negative particles were obtained (Table A1 in Appendix). Furthermore, the particles produced were characterized by high conversion and low polydispersity index, as expected for particles synthesized via FRPe. In particular, CTAB was chosen as surfactant because its long hydrocarbon chain should favor hydrophobic interactions strong enough to prevent possible desorption when the particles come into contact with the negatively charged hair. Actually, we verified that this is not the case in the case of particles made of high-Tg polymer such as MMA-CTAB1 particles. These particles were in fact subject to fast aggregation as soon as put in contact with hair, as shown by the increasing average particle size and PDI during time shown in FIG. 9a. Therefore, given the clear connection between particle stability and addition of hair, a mechanism of emulsifier displacement from the particle surface by hair can be expected. In order to better clarify this phenomenon, ξ-potential has been measured all along the experiment and plotted as a function of time, as shown in FIG. 9b. The decreasing values of ξ-potential are a convincing indication of the possible migration of the surfactant molecules from the particles to the hair surface. Such depletion of emulsifier reduces the electrostatic repulsion among the particles, thus resulting in particle aggregation with increasing average size and broadening of the size distribution. To further support this explanation, batch adsorption experiments using hair previously loaded with the emulsifier (equilibrated with a 1% w/w solution of CTAB) were carried out, as shown in FIG. 10. No particle aggregation happens in this case (cf. FIG. 10a). Since pre-saturated hair are no longer abstracting emulsifier from the particle surface, the particle dispersion remains stable enough. Nevertheless, the same pre-saturation provide significant positive surface charge on hair, thus creating an electrostatic repulsion towards particles with the same charge: in fact, the amount of adsorbed particles per unit mass of hair is strongly reduced, as indicated by the values reported as a function of time in FIG. 10b. These values of particle loading are comparable to those measured in the case of the least adsorbing sample MPC-BMA (FIG. 4b).

Figure 10C:
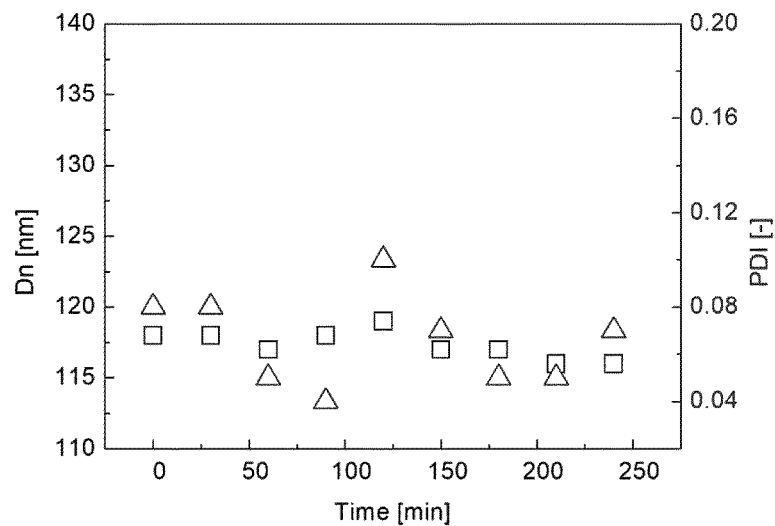

On the contrary, particles made of low-Tg polymer proved to be stable all along the adsorption experiment, as reported in FIG. 10c, showing almost constant size and PDI for the sample BMA-CTAB3. The adsorption kinetics at different particle concentration is finally reported in Figure A4 in Appendix. A significant amount of adsorbed polymer (i.e. up to 23 mg/g) can be recorded in the case of highly positive particles with low Tg. However, some destabilization was recorded when using the smallest concentration (0.2 mg/ml): a slight increase in average size when put in contact with hair was noticed (data not shown), indicating that the same mechanism of emulsifier abstraction could be active also in the case of BMA-based particles at least at lower extent.

Comparing the results of the last previous experiments, some additional comments are relevant. Indeed, an increase in the concentration of the particles corresponds to an increase in the overall amount of emulsifier that can be abstracted by hair. Therefore, if the particle concentration is large enough, a smaller reduction of ξ-potential is achieved, thus ensuring better colloidal stabilization. On the other hand, the impact of the emulsifier abstraction is strongly dependent upon the polymer type. BMA-based particles were by far less prone to aggregation, thus exhibiting similar adsorption kinetics. Since average particle size and initial emulsifier coverage of the two samples, MMA-CTAB1 and BMA-CTAB3, are very similar, the different behavior can be explained considering the lower Tg and the higher hydrophobicity of pBMA with respect to pMMA. In fact, some partial interpenetration of the hydrocarbon chain of the CTAB could take place only in the case of the former, softer polymer: such interpenetration should make the migration of the emulsifier much less probable than in the case of the rigid pMMA. This feature, along with the larger adsorption ability at lower Tg already mentioned in the case of moderately charged particles, may be considered a decisive advantage of pBMA-based polymers.

In FIG. 11, the adsorption isotherms of sample BMA-CTAB1 in distilled and tap water, respectively, are shown. As in the case of the moderately negative particles (sample MPC-BMA1, FIG. 6), the adsorbed concentrations increase at increasing particle concentration in the liquid phase. This behavior is very slightly affected by the medium composition, suggesting that the ions present in the tap water play only a minor role. However, the amount of particles adsorbed on hair is significantly larger than that measured in the case of the sample MPC-BMA1, confirming the key role of the surface charge in determining the adsorption extent.

Furthermore, as for the BMA-MPC particles, the impact of the particle size has been evaluated as depicted in FIG. 12, where the values of adsorbed amount of polymer at equilibrium with an initial particle concentration of 1 mg/ml is reported as a function of the average particle diameter. In accordance with the results previously shown in FIG. 5 for negatively charged particles, Qe is decreasing at increasing particle size also in the case of positive particles, again explained by the higher surface to volume ratio at decreasing particle size. Therefore, it can be argued that particle size is a control variable to tune the adsorption of colloids on hair.

3.4 Influence of Surface Charge Over Particle Adsorption particles with similar diameter ξ200 nm), low Tg (BMA-based) but different surface charge (namely ~−40, ~−20 and ~+40 mV, as depicted in FIG. 13) were finally selected to directly relate the latter property to the particle adsorption on hair. As depicted in FIG. 14, in which the adsorption kinetics of the three colloids are shown, the surface charge of the particles plays a determinant role. Indeed, a clear impact of the ξ-potential on the final value of $Q_e$ can be observed, with the positive particles interacting the most with the hair surface. As already discussed, this is attributed to the favorable electrostatic interactions between the overall negatively charged hair and the positively charge particles, which enhances significantly the adsorption of these colloids on hair.

4. CONCLUSIONS

The results show that particle size, surface charge and glass transition temperature of the polymer have an important bearing on the substantivity of particles on hair. It was found that the smaller are the particles, the higher are the adsorbed amounts at equilibrium. This behavior was attributed to the increased particle specific surface with decreasing particle size. Moreover, it was shown that the surface charge is a key parameter: the more positive are the particles, the greater is the adsorption on hair. This is most likely due to the overall negative charge on the hair surface, which brings about electrostatic attraction as an important driving force in the particle adsorption.

Neutral particles stabilized by a steric surfactant like PEG are not at all adsorbing. Finally, the lower the value of the glass transition temperature of the polymer, the more favorable the adsorption. This is probably due to the larger mobility of the macromolecules constituting the polymer matrix, which results in better adhesion on hair surface.

The invention claimed is:

1. A fragrance-containing microparticle of water-insoluble polymeric material selected from 2-methacryloyloxyethylphosphorylcholine homopolymers and copolymers of methyl methacrylate with 2-methacryloyloxyethylphosphorylcholine, the polymer having a glass transition temperature of from 0° C. to 50° C. and a zeta potential within the range −40 mV to −5 mV or +5 mV to +45 mV.

2. The fragrance-containing microparticle according to claim 1, wherein the glass transition temperature is within the range 20° C. to 40° C.

3. The fragrance-containing microparticle according to claim 1, wherein the zeta-potential is within the range +30 mV to +45 mV.

4. The fragrance-containing microparticle according to claim 1, wherein the polymer is a copolymer of methyl methacrylate and 2-methacryloyloxyethylphosphorylcholine, and wherein the methyl methacrylate (MMA) monomer content comprises 20% by weight maximum.

5. The fragrance-containing microparticle according to claim 1, wherein the glass transition temperature is within the range 20° C. to 30° C.

6. The fragrance-containing microparticle according to claim 1, wherein the polymer is a copolymer of methyl methacrylate and 2-methacryloyloxyethylphosphorylcholine, and wherein the methyl methacrylate (MMA) monomer content comprises 15% by weight maximum.

7. The fragrance-containing microparticle according to claim 1, wherein the polymer is a copolymer of methyl methacrylate and 2-methacryloyloxyethylphosphorylcholine, and wherein the methyl methacrylate (MMA) monomer content comprises 10% by weight maximum.

8. The fragrance-containing microparticle according to claim 1, wherein the polymer is a copolymer of methyl methacrylate and 2-methacryloyloxyethylphosphorylcholine, and wherein the methyl methacrylate (MMA) monomer content comprises 5% by weight maximum.

9. A rinse-off hair care composition comprising the fragrance-containing microparticle of claim 1.

10. A method of achieving a long-term fragrancing of hair, comprising applying the rinse-off hair care composition according to claim 9.

* * * * *